US012708800B2

(12) United States Patent
Li et al.

(10) Patent No.: US 12,708,800 B2
(45) Date of Patent: Aug. 18, 2026

(54) ULTRASOUND TREATMENT DEVICE, CONTROL METHOD AND STORAGE MEDIUM THEREOF

(71) Applicant: SHENZHEN PENINSULA MEDICAL GROUP, Shenzhen (CN)

(72) Inventors: Yanan Li, Shenzhen (CN); Shuyun Hu, Shenzhen (CN); Xiaobing Lei, Shenzhen (CN); Yi Ding, Shenzhen (CN)

(73) Assignee: SHENZHEN PENINSULA MEDICAL GROUP, Shenzhen (CN)

( * ) Notice: Subject to any disclaimer, the term of this patent is extended or adjusted under 35 U.S.C. 154(b) by 0 days.

(21) Appl. No.: 18/726,952

(22) PCT Filed: Dec. 27, 2023

(86) PCT No.: PCT/CN2023/142427
§ 371 (c)(1),
(2) Date: Jul. 5, 2024

(87) PCT Pub. No.: WO2024/140828
PCT Pub. Date: Jul. 4, 2024

(65) Prior Publication Data

US 2025/0090870 A1 Mar. 20, 2025

(30) Foreign Application Priority Data

Dec. 30, 2022 (CN) ......................... 202211727234.7

(51) Int. Cl.
*A61N 7/00* (2006.01)

(52) U.S. Cl.
CPC ........ *A61N 7/00* (2013.01); *A61N 2007/0034* (2013.01)

(58) Field of Classification Search
CPC .............. A61N 7/00; A61N 2007/0004; A61N 2007/0008; A61N 2007/0034; A61N 2007/0082; A61B 8/429
See application file for complete search history.

(56) References Cited

U.S. PATENT DOCUMENTS 6,183,426 B1 2/2001 Akisada et al.
2013/0338545 A1 12/2013 Azhari et al.
(Continued)

FOREIGN PATENT DOCUMENTS

CN 1222846 A 7/1999
CN 105407824 A 3/2016
(Continued)

OTHER PUBLICATIONS

International Search Report and Written Opinion issued in corresponding PCT Application No. PCT/CN2023/142427, dated Apr. 10, 2024.
(Continued)

*Primary Examiner* — Carolyn A Pehlke
(74) *Attorney, Agent, or Firm* — Westbridge IP LLC

(57) ABSTRACT

Disclosed are a control method for an ultrasound treatment device including an ultrasound treatment tip, a control method and a storage medium thereof. The control method includes: determining whether the ultrasound treatment tip moves according to current displacement data of the ultrasound treatment tip collected by the displacement sensor; determining a contact state between the ultrasound treatment tip and the human skin according to the current contact data of the ultrasound treatment tip collected by the contact sensor; and controlling the ultrasound treatment tip to start or stop outputting the ultrasound energy according to the current displacement data and the current contact data.

6 Claims, 2 Drawing Sheets

(56) References Cited

U.S. PATENT DOCUMENTS

| | | | | |
|---|---|---|---|---|
| 2015/0174388 | A1* | 6/2015 | Slayton | A61M 37/0092 604/22 |
| 2015/0360058 | A1* | 12/2015 | Barthe | A61N 7/02 606/27 |
| 2022/0218563 | A1* | 7/2022 | Camozzi | A61H 23/0236 |
| 2022/0288426 | A1 | 9/2022 | Slayton | |
| 2023/0414299 | A1* | 12/2023 | Khuri-Yakub | A61B 8/4494 |
| 2024/0108307 | A1* | 4/2024 | Ebata | A61B 8/461 |

FOREIGN PATENT DOCUMENTS

| | | | |
|---|---|---|---|
| CN | 106563212 | A | 4/2017 |
| CN | 206499788 | U | 9/2017 |
| CN | 114425130 | A | 5/2022 |
| CN | 216603841 | U | 5/2022 |
| CN | 114949640 | A | 8/2022 |
| CN | 116159254 | A | 5/2023 |
| JP | H09248213 | A | 9/1997 |
| JP | H10263039 | A | 10/1998 |
| JP | 2000312703 | A | 11/2000 |
| JP | 3816960 | B2 | 8/2006 |
| KR | 20090078619 | A | 7/2009 |
| WO | 2022270180 | A1 | 12/2022 |

OTHER PUBLICATIONS

Decision to Grant a Patent issued in counterpart Japanese Patent Application No. JP 2025-514857, dated Mar. 10, 2026.

Notice of Reasons for Refusal issued in counterpart Japanese Patent Application No. 2025-514857, dated Oct. 7, 2025.

European Search Report issued in counterpart European Patent Application No. EP 23910746.9, dated Jun. 29, 2026.

First Office Action issued in counterpart Chinese Patent Application No. 202211727234.7, dated May 30, 2026.

* cited by examiner

ULTRASOUND TREATMENT DEVICE, CONTROL METHOD AND STORAGE MEDIUM THEREOF

CROSS-REFERENCE TO RELATED APPLICATIONS

The present application is a national stage filing under 35 U.S.C § 371 of International Application No. PCT/CN2023/142427, filed on Dec. 27, 2023, which claims priority to Chinese Patent Application No. 202211727234.7, filed on Dec. 30, 2022, the entire contents of which are incorporated herein by reference.

TECHNICAL FIELD

The present application relates to an ultrasound treatment tip, an ultrasound treatment device, a control method and a storage medium thereof.

BACKGROUND

In related art, when using an ultrasound treatment device, if the ultrasound treatment tip continues to treat a point underneath the skin, it can easily cause the skin to be burned. Therefore, it is necessary to equip the ultrasound treatment tip with a contact sensor. As long as the contact sensor detects contact between the ultrasound treatment tip and the skin, the ultrasound treatment tip will continue to be controlled to output energy.

However, when the contact sensor detects contact between the ultrasound treatment tip and the skin and the ultrasound treatment device stops moving, the ultrasound treatment device still determines that the ultrasound treatment tip is in continuous use, thereby controlling the ultrasound treatment tip to continue emitting energy, which may easily cause burns to the user, indicating that the existing contact detection accuracy of the ultrasound treatment tip is not high.

SUMMARY

The main objective of the present application is to provide a control method for an ultrasound treatment device including an ultrasound treatment device, and a storage medium, aiming to solve the existing technical problem of low relative displacement detection accuracy of the ultrasound treatment tip.

In a first aspect, in order to achieve the above objective, the present application provides a control method for an ultrasound treatment device including an ultrasound treatment tip, a displacement sensor, and a contact sensor.

The ultrasound treatment tip is configured to output ultrasound energy.

The displacement sensor is provided on the ultrasound treatment tip or a handle portion of the ultrasound treatment device, and is configured to collect displacement data of the ultrasound treatment tip.

The contact sensor is provided on the ultrasound treatment tip and is configured to collect current contact data between the ultrasound treatment tip and corresponding human skin.

The method includes:

determining whether the ultrasound treatment tip moves according to current displacement data of the ultrasound treatment tip collected by the displacement sensor;

determining a contact state between the ultrasound treatment tip and the human skin according to the current contact data of the ultrasound treatment tip collected by the contact sensor; and controlling the ultrasound treatment tip to start or stop outputting the ultrasound energy according to the current displacement data and the current contact data.

In an embodiment, the contact sensor includes a pressure sensor, and the current contact data of the ultrasound treatment tip is current pressure data collected by the pressure sensor.

In an embodiment, the determining the contact state between the ultrasound treatment tip and the human skin according to the current contact data of the ultrasound treatment tip collected by the contact sensor includes:

determining whether the current pressure data is greater than or equal to a preset pressure value;

in response to determining that the current pressure data is greater than or equal to a preset pressure value, and the current displacement data is greater than 0, controlling the ultrasound treatment tip to output the ultrasound energy.

In an embodiment, the determining the contact state between the ultrasound treatment tip and the human skin according to the current contact data of the ultrasound treatment tip collected by the contact sensor includes:

generating a pressure change curve according to historical pressure data collected by the pressure sensor and the current pressure data; and determining whether the ultrasound treatment tip slides in a treatment area according to the pressure change curve.

In an embodiment, the determining whether the ultrasound treatment tip slides in the treatment area according to the pressure change curve includes:

selecting multiple continuous pressure data including the current pressure data from the pressure change curve;

in response to the multiple continuous pressure data being at least partially different, determining that the ultrasound treatment tip slides in the treatment area and the current displacement data is greater than 0, and controlling the ultrasound treatment tip to output the ultrasound energy; and in response to the multiple continuous pressure data being the same, determining that the ultrasound treatment tip does not slide in the treatment area, and controlling the ultrasound treatment tip to stop outputting the ultrasound energy.

In an embodiment, the determining the contact state between the ultrasound treatment tip and the human skin according to the current contact data of the ultrasound treatment tip collected by the contact sensor includes:

determining a pressure difference between any two adjacent moments within a preset time period to obtain at least two pressure change values according to the historical pressure data collected by the pressure sensor and the current pressure data; and determining whether the ultrasound treatment tip slides in the treatment area according to the at least two pressure change values.

In an embodiment, the determining whether the ultrasound treatment tip slides in the treatment area according to the at least two pressure change values includes:

in response to all the pressure change values being zero, determining that the ultrasound treatment tip does not slide in the treatment area; and controlling the ultrasound treatment tip to stop outputting the ultrasound energy.

In an embodiment, the determining whether the ultrasound treatment tip moves according to the current displacement data of the ultrasound treatment tip collected by the displacement sensor includes:

obtaining a moving speed value of the ultrasound treatment tip;

determining whether the moving speed value is greater than or equal to a preset moving speed value; and in response to the moving speed value being greater than or equal to the preset moving speed value, determining that the ultrasound treatment tip moves.

In a second aspect, the present application further provides an ultrasound treatment device including: an ultrasound treatment tip, a displacement sensor, a contact sensor, a processor, a memory, and a controller controlling the ultrasound treatment tip to start or stop outputting the ultrasound energy based on the control method based on the aforementioned method.

The ultrasound treatment tip configured to output ultrasound energy.

The displacement sensor provided on the ultrasound treatment tip or a handle portion of the ultrasound treatment device, and configured to collect the displacement data of the ultrasound treatment tip.

The contact sensor provided on the ultrasound treatment tip and configured to collect current contact data between the ultrasound treatment tip and corresponding human skin.

When the control program for the ultrasound treatment device is executed by the processor, steps of the control method for the ultrasound treatment device according to the first aspect are operated.

In a third aspect, the present application further provides a computer-readable storage medium. The computer-readable storage medium stores a control program for the ultrasound treatment device. When the control program for the ultrasound treatment device is executed by a processor, the control method for the ultrasound treatment device as described in the first aspect is operated.

In the control method for the ultrasound treatment device provided in the embodiment of the present application, the displacement data of the ultrasound treatment tip and the current contact data are obtained; whether the ultrasound treatment tip moves is determined according to the displacement data of the ultrasound treatment tip; In response to that the ultrasound treatment tip moves, the contact state between the ultrasound treatment tip and the human skin is determined according to the current contact data; the ultrasound treatment tip is controlled to start or stop outputting the ultrasound energy according to the displacement data and the pressure data.

Therefore, in an embodiment, after the ultrasound treatment device obtains the displacement data of the ultrasound treatment tip through the displacement sensor, the displacement data of the ultrasound treatment tip is compared with the preset displacement data, and at the same time whether the ultrasound treatment tip moves is determined, and the contact state between the ultrasound treatment tip and human skin is determined according to the current contact data obtained by the contact sensor. That is, the present application uses a displacement sensor in combination with a contact sensor to determine the contact state between the ultrasound treatment tip and human skin from multiple dimensions, and control the ultrasound treatment tip to start or stop outputting ultrasound energy, which is beneficial to improving the safety of using ultrasound treatment device.

The realization of the purpose, functional features and advantages of the present application will be further described with reference to the embodiments and the accompanying drawings.

DETAILED DESCRIPTION OF THE EMBODIMENTS

It should be understood that the specific embodiments described here are only used to explain the present application and are not used to limit the present application.

In related art, when using an ultrasound treatment device, if the ultrasound treatment tip constantly treats one same point under the skin, it can easily cause the skin get burned. Therefore, it is necessary to equip the ultrasound treatment tip or the untrasound treatment device with a displacement sensor. As long as the ultrasound treatment tip is detected to move, the treatment can be turned on, otherwise the transducer can be turned off.

However, there are certain loopholes in this manner. For example, when the user uses the ultrasound treatment tip by himself, if the user himself drives the entire ultrasound treatment device to move, the ultrasound treatment tip does not move relative to the skin surface; but at this time the system will also determine that the ultrasound treatment tip is moving relative to the skin surface, and the transducer will continue to run, causing burns to the user. That is, the relative displacement detection accuracy of the existing ultrasound treatment tip is not high.

The present application provides a solution. In the embodiment, after the ultrasound treatment device obtains the displacement data from the ultrasound treatment tip through the displacement sensor, the displacement data of the ultrasound treatment tip is compared with the preset displacement data, and after the ultrasound treatment tip is determined to move, the contact state between the ultrasound treatment tip and human skin is determined according to the current contact data obtained by the contact sensor. That is, the present application uses the displacement sensor in combination with the contact sensor to determine the contact state between the ultrasound treatment tip and human skin from multiple dimensions, thereby improving the determination accuracy, realizing controlling the ultrasound treatment tip to output ultrasound energy in time, which is beneficial to improving the safety of using ultrasound treatment device.

The ultrasound treatment device applied in the embodiments of the present application will be described as follows.

Figure 1:
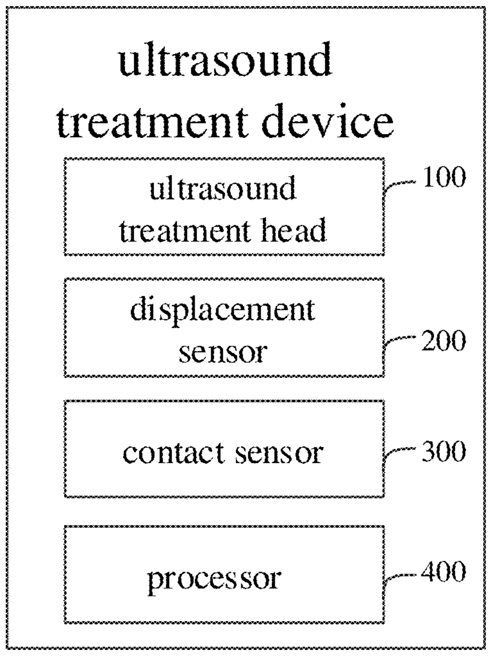
FIG. 1 is a schematic structural diagram of a radio frequency array control device according to a first embodiment of the present application.

The present application provides a first embodiment of a control device for an ultrasound treatment device. As shown in FIG. 1, which is a schematic structural diagram of a radio frequency array control device according to a first embodiment of the present application.

It should be noted that although a logical sequence is shown in the flowcharts, in some cases, the steps shown or described may be performed in a sequence different from that herein.

In the first embodiment, the ultrasound treatment device includes: an ultrasound treatment tip 100, a displacement sensor 200, a contact sensor 300, and a processor 400, a controller, the controller includes a memory, and a control program for the ultrasound treatment device stored in the memory.

The ultrasound treatment tip 100 is configured to output ultrasound energy.

The displacement sensor 200 is provided on the ultrasound treatment tip or a handle portion of the ultrasound treatment device and is configured to collect displacement data of the ultrasound treatment tip of the ultrasound treatment tip.

The contact sensor 300 is provided on the ultrasound treatment tip and is configured to collect current contact data between the ultrasound treatment tip and corresponding human skin.

When the control program for the ultrasound treatment tip is executed by the processor, the steps of the control method for the ultrasound treatment device are operated.

In some embodiments, the contact sensor includes a pressure sensor, a capacitive sensor or an infrared ranging sensor. The type of the contact sensor is not limited here, and at least one contact sensor is required.

Figure 2:
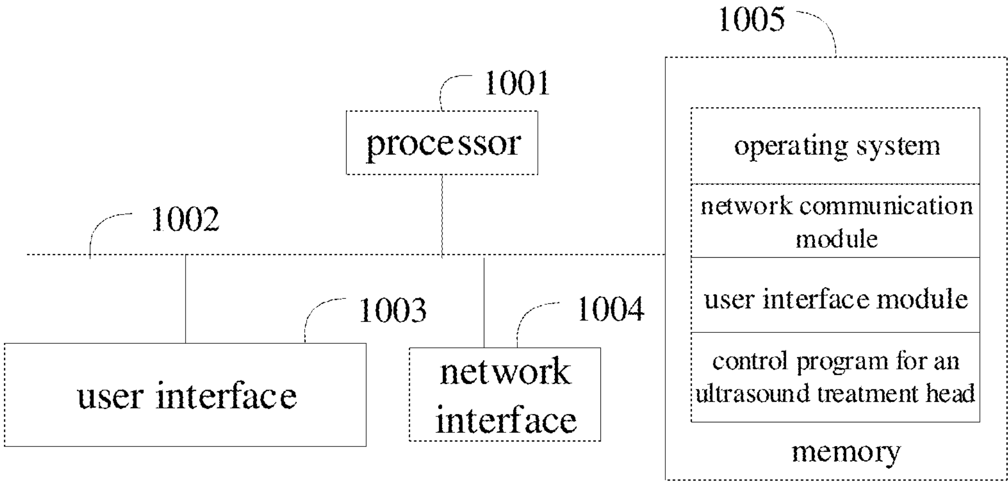
FIG. 2 is a schematic structural diagram of an ultrasound treatment device of the hardware operating environment involved in the present application.

As shown in FIG. 2, which is schematic structural diagram of an ultrasound treatment device of the hardware operating environment involved in the embodiments of the present application.

As shown in FIG. 2, the ultrasound treatment device may include: a processor 1001, such as a center processing unit (CPU), a communication bus 1002, a user interface 1003, a network interface 1004, and a memory 1005. The communication bus 1002 is configured to realize connection communication between these components. The user interface 1003 may include a display screen and an input unit such as a keyboard. In an embodiment, the user interface 1003 may also include a standard wired interface and a wireless interface. The network interface 1004 may include a standard wired interface or a wireless interface (such as a wireless fidelity (Wi-Fi) interface). The memory 1005 may be a high-speed random access memory (RAM) or a stable memory (non-volatile memory (NVM)), such as a disk memory. The memory 1005 may be a storage apparatus independent of the aforementioned processor 1001.

Those skilled in the art can understand that the terminal structure shown in FIG. 2 does not limit the ultrasound treatment device, and may include more or fewer components than shown, or combine certain components, or include different components arrangement.

As shown in FIG. 2, memory 1005, which is a computer storage medium, may include an operating system, a network communication module, a user interface module and a control program for the ultrasound treatment device. In an embodiment, the control program is also configured for controlling the ultrasound treatment tip 100.

In the ultrasound treatment device shown in FIG. 2, the network interface 1004 is mainly configured for data communication with the network server. The user interface 1003 is mainly configured for data interaction with the user. The processor 1001 and the memory 1005 can be provided in the ultrasound treatment device, the ultrasound treatment device is configured to call the control program for the ultrasound treatment device stored in memory 1005 through the processor 1001 and execute the control method for the ultrasound treatment device according to the embodiment of the present application.

Figures 3, 4:
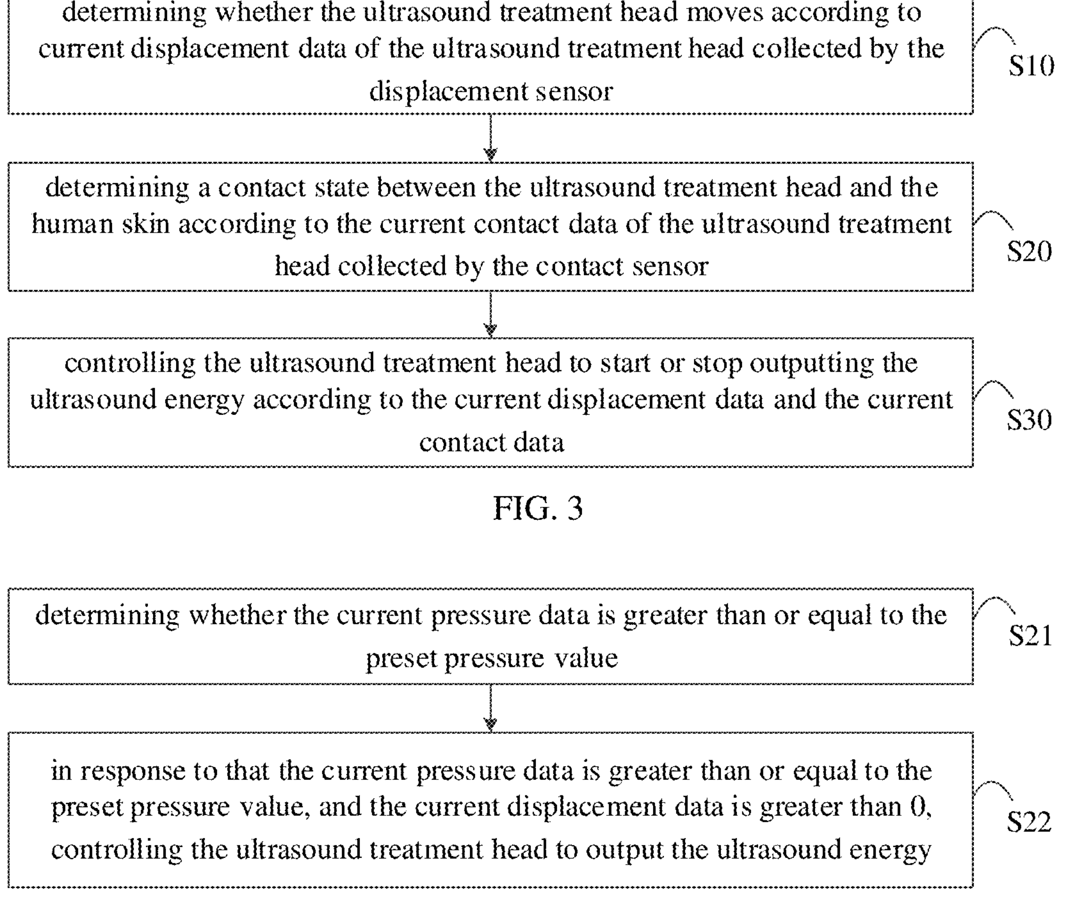
FIG. 3 is a schematic flowchart of a control method for an ultrasound treatment device according to the first embodiment of the present application.
FIG. 4 is a schematic flowchart of the control method for the ultrasound treatment device according to a second embodiment of the present application.

Based on the hardware structure of the above-mentioned ultrasound treatment device but not limited to the above-mentioned hardware structure, the present application provides a first embodiment of a control method for an ultrasound treatment device. As shown in FIG. 3, which shows a schematic flowchart of the control method for the ultrasound treatment device according to the first embodiment of the present application.

It should be noted that although a logical sequence is shown in the flowcharts, in some cases, the steps shown or described may be performed in a sequence different from that herein.

In the embodiment, the ultrasound treatment device includes:

The present application provides a control method for the ultrasound treatment device including an ultrasound treatment tip 100, a displacement sensor 200, and a contact sensor 300.

The ultrasound treatment tip 100 is configured to output ultrasound energy.

The displacement sensor 200 is provided on the ultrasound treatment tip 100 or a handle portion of the ultrasound treatment device and is configured to collect the displacement data of the ultrasound treatment tip 100.

The contact sensor 300 is provided on the ultrasound treatment tip 100 and is configured to collect current contact data between the ultrasound treatment tip 100 and corresponding human skin.

The control method includes steps S10 to S30:

S10, determining whether the ultrasound treatment tip moves according to current displacement data of the ultrasound treatment tip collected by the displacement sensor.

It can be understood that the execution subject of the embodiment is the ultrasound treatment device. The displacement data of the ultrasound treatment tip is specifically the spatial movement data of the ultrasound treatment tip when the user is using the ultrasound treatment device. The ultrasound treatment device collects the displacement data of the ultrasound treatment tip through a displacement sensor.

The current contact data specifically refers to the contact data between the ultrasound treatment tip and human skin when the user is using the ultrasound treatment device. The ultrasound treatment device collects the current contact data through the contact sensor. The contact sensor includes pressure sensors and capacitive sensors, or infrared ranging sensor.

It can be understood that the ultrasound treatment device collects the displacement data of the ultrasound treatment tip through a displacement sensor, that is, the displacement sensor monitors whether the ultrasound treatment tip moves. If the displacement data of the ultrasound treatment tip collected by the displacement sensor is zero, it is determined that the ultrasound treatment tip is continuously treating one point on the human skin. At this time, it is easy to cause the user's skin to be burned.

S20, determining a contact state between the ultrasound treatment tip and the human skin according to the current contact data of the ultrasound treatment tip collected by the contact sensor.

It can be understood that the ultrasound treatment tip moves in space, that is, the displacement data greater than 0 does not mean that the ultrasound treatment tip is in contact with the human skin. For example, when the user drives the entire ultrasound treatment device to move, if the ultrasound treatment tip is not in contact with the human skin at this time or is located at a certain point on the human skin for a long time, it will also cause the ultrasound treatment tip to move in the space, and the displacement sensor can also detect displacement data greater than 0 at this time. Therefore, in order to more accurately determine the status of the ultrasound treatment tip, it is necessary to collect the current contact data between the ultrasound treatment tip and human skin at the same time.

It can be understood that when the user moves the ultrasound treatment tip, the ultrasound treatment tip is in contact with the human skin, that is, the ultrasound treatment tip and the human skin must be in contact. At this time, the contact sensor will inevitably detect the contact data. Therefore, the ultrasound treatment device collects contact data between the ultrasound treatment tip and human skin according to the contact sensor. While collecting movement data of the ultrasound treatment tip, the contact status between the ultrasound treatment tip and human skin is determined.

S30, controlling the ultrasound treatment tip to start or stop outputting the ultrasound energy according to the current displacement data and the current contact data.

It can be understood that the ultrasound treatment tip includes a stopping state and a starting state. When the ultrasound treatment tip is in the stopping state, the ultrasound treatment tip does not output the ultrasound energy; when the ultrasound treatment tip is in the starting state, the ultrasound treatment tip outputs the ultrasound energy. After the ultrasound treatment device determines that there is contact between the ultrasound treatment tip and human skin, the ultrasound treatment device controls the ultrasound treatment tip to output the ultrasound energy.

In the embodiment, the ultrasound treatment device can obtain the current displacement data of the ultrasound treatment tip through the displacement sensor, and at the same time obtain the current contact data of the ultrasound treatment tip through the contact sensor. The ultrasound treatment device controls the start or stop of the ultrasound treatment tip according to the current displacement data and the current contact data. The displacement data of the ultrasound treatment tip is compared with the preset displacement data to determine that the ultrasound treatment tip moves. The contact status between the ultrasound treatment tip and human skin is determined according to the current contact data obtained by the contact sensor. The comparison of the current displacement data and the current contact data is not sequential, that is, the present application uses the displacement sensor and the contact sensor simultaneously to determine the contact state between the ultrasound treatment tip and human skin from multiple dimensions, which is conducive to more accurately determining the role of the ultrasound treatment tip. The working state of human skin can control the ultrasound treatment tip to output the ultrasound energy, which is beneficial to improving the safety of using the ultrasound treatment device.

The contact sensor includes a pressure sensor, and the current contact data is the current pressure data collected by the pressure sensor.

In an embodiment, the contact sensor includes a pressure sensor, and the current contact data of the ultrasound treatment tip is the current pressure data collected by the pressure sensor.

It can be understood that the contact sensor includes a pressure sensor, and the pressure sensor can be used to collect the current pressure data between the current ultrasound treatment tip and human skin. The ultrasound treatment device can determine the contact state between the ultrasound treatment tip and human skin according to the current pressure data collected by the pressure sensor.

In an embodiment, after the ultrasound treatment tip moves, the ultrasound treatment device determines the contact state between the ultrasound treatment tip and human skin according to the current pressure data collected by the pressure sensor, which is conducive to more accurately determining the contact state between the ultrasound treatment tip and human skin, and controlling the ultrasound treatment tip to output the ultrasound energy, which is beneficial to improving the safety of using the ultrasound treatment device.

Based on the above embodiments, the present application provides a second embodiment of the control method for the ultrasound treatment device. As shown in FIG. 4, which shows a schematic flowchart of the control method for the ultrasound treatment device according to a second embodiment of the present application.

In the embodiment, step S20 further includes:

S21, determining whether the current pressure data is greater than or equal to the preset pressure value; and

S22, in response to that the current pressure data is greater than or equal to the preset pressure value, and the current displacement data is greater than 0, controlling the ultrasound treatment tip to output the ultrasound energy.

It can be understood that the preset pressure value is a value preset by the user. After the pressure sensor obtains the current pressure data, the ultrasound treatment device uses the preset pressure value to compare with the current pressure data collected by the pressure sensor. In response to that the current pressure data is greater than or equal to the preset pressure value, it means that the ultrasound treatment tip is in contact with the human skin at this time. The contact between the ultrasound treatment device and the ultrasound treatment tip is good, and the ultrasound treatment device controls the ultrasound treatment tip to output ultrasound energy. In the embodiment, the ultrasound treatment device compares the current pressure data with the preset pressure value, which is beneficial to accurately determining whether the contact between the ultrasound treatment tip and the human skin is good, thereby realizing accurate control of the ultrasound energy output of the ultrasound treatment tip. In the embodiment, once the current pressure data shows a poor contact state, that is, the current pressure data is less than the preset pressure value, the ultrasound treatment tip should be controlled immediately to stop outputting the ultrasound energy, so that the safety of using the ultrasound treatment device is improved.

In an embodiment, step S20 specifically includes:

generating a pressure change curve according to historical pressure data collected by the pressure sensor and the current pressure data; determining whether the ultrasound treatment tip slides in a treatment area according to the pressure change curve;

selecting multiple continuous pressure data including the current pressure data from the pressure change curve;

in response to the multiple continuous pressure data being at least partially different, determining that the ultrasound treatment tip slides in the treatment area and the current displacement data is greater than 0, and controlling the ultrasound treatment tip to output the ultrasound energy; and in response to the multiple continuous pressure data being the same, determining that the ultrasound treatment tip does not slide in the treatment area, and controlling the ultrasound treatment tip to stop outputting the ultrasound energy.

It is understandable that since the pressure sensor can only collect current pressure data, when the user uses the ultrasound treatment device, after the pressure sensor continuously collects pressure data, the ultrasound treatment device will store the pressure data in the memory as historical pressure data. At this time, the ultrasound treatment device can generate the pressure change curve according to the historical pressure data and the current pressure data collected by the pressure sensor. The ultrasound treatment device determines multiple pressure data from the pressure change curve, the multiple pressure data includes the current pressure data. When the multiple pressure data are at least partially different, it is determined that the ultrasound treatment tip slides in the treatment area; when the multiple pressure data are the same, it is determined that the ultrasound treatment tip does not slide in the treatment area. At this time, the ultrasound treatment tip may stay at a certain position on the human skin for a long time. Even if the current displacement data may be greater than 0, it is still possible that the user holds the ultrasound treatment tip to move and the ultrasound treatment tip stays in a certain position on the human skin for a long time. At this time, it is necessary to immediately control the ultrasound treatment tip to stop outputting energy to avoid the user being burned. If the ultrasound treatment tip slides in the treatment area and the displacement data collected at this time is greater than 0, that is, the ultrasound treatment tip is in normal use, and the ultrasound treatment tip is controlled to output the ultrasound energy at this time.

In an embodiment, after the ultrasound treatment device generates a pressure change curve through historical pressure data and current pressure data, it can intuitively determine whether the current pressure data is fluctuating within the pressure change curve, and whether the ultrasound treatment tip slides in the treatment area. If the ultrasound treatment tip moves in the treatment area, that is, when the ultrasound treatment tip is in normal use, it can accurately control the ultrasound energy output of the ultrasound treatment tip. It can be understood that using other similar data processing methods to determine whether the ultrasound treatment tip slides in the treatment area according to the pressure change curve also falls within the protection scope of the embodiment.

As a specific embodiment, in an embodiment, step S20 further includes:

determining a pressure difference between any two adjacent moments within a preset time period to obtain at least two pressure change values according to the historical pressure data collected by the pressure sensor and the current pressure data; and determining whether the ultrasound treatment tip slides in the treatment area according to the at least two pressure change values.

It can be understood that the preset time period can be set according to the authorized user. For example, the preset time period can be 1 minute or 5 minutes. There is no limit to the preset time period here. The pressure change value is the pressure difference between any two adjacent moments within the preset time period. The pressure change values include at least two, and may also include multiple pressure change values. The quantity of pressure change values is not limited here. The ultrasound treatment device can determine whether the ultrasound treatment tip slides in the treatment area according to the at least two pressure change values.

In an embodiment, the ultrasound treatment device determines whether the ultrasound treatment tip slides in the treatment area according to the at least two pressure change values, and can more accurately determine whether the ultrasound treatment tip is in use.

As a specific embodiment, in an embodiment, the step of determining whether the ultrasound treatment tip slides in the treatment area according to the at least two pressure change values specifically includes:

in response to all the pressure change values being zero, determining that the ultrasound treatment tip does not slide in the treatment area; and controlling the ultrasound treatment tip to stop outputting the ultrasound energy.

It can be understood that when the ultrasound treatment tip determines that all pressure change values are zero, the pressure does not change within the preset time period. Then the ultrasound treatment device determines that the ultrasound treatment tip does not slide in the treatment area and needs to be controlled immediately to stop outputting ultrasound energy to ensure user safety. If all pressure change values are not zero, it means that the pressure has changed within the preset time period, thereby determining that the ultrasound treatment device slides in the treatment area, at this time, the ultrasound treatment tip is controlled to output the ultrasound energy.

For example, when the user is using the ultrasound treatment tip and walking, the displacement sensor collects the displacement data of the ultrasound treatment tip. At this time, according to the pressure data collected by the pressure sensor, the ultrasound treatment device determines that the multiple continuous pressure change value is zero, it is determined that the ultrasound treatment tip does not slide in the treatment area, and the ultrasound treatment device immediately controls the ultrasound treatment tip to stop outputting ultrasound energy.

In an embodiment, the ultrasound treatment device determines whether all pressure change values are zero, which is conducive to accurately determining whether the ultrasound treatment tip slides in the treatment area, thereby achieving accurate control of the ultrasound treatment tip.

As a specific embodiment, in an embodiment, step S10 specifically includes:

obtaining a moving speed value of the ultrasound treatment tip;

determining whether the moving speed value is greater than or equal to a preset moving speed value; and in response to the moving speed value being greater than or equal to the preset moving speed value, determining that the ultrasound treatment tip moves.

It can be understood that the displacement sensor can collect the moving speed value of the ultrasound treatment tip, and the preset moving speed value is a value preset by an authorized user. The ultrasound treatment device determines whether the ultrasound treatment tip is effectively moving by determining whether the moving speed value is greater than or equal to the preset moving speed value. If the moving speed value is greater than or equal to the preset moving speed value, it is determined that the ultrasound treatment tip moves effectively. If the moving speed value is less than the preset moving speed value, it is determined that the ultrasound treatment tip does not move effectively.

In the embodiment, the ultrasound treatment device can more accurately determine whether there is effective movement of the ultrasound treatment tip by determining whether the moving speed value is greater than or equal to the preset moving speed value.

In addition, embodiments of the present application further provide a computer-readable storage medium, where a control program for the ultrasound treatment tip is stored. When the control program for the ultrasound treatment tip is executed by the processor, the steps of the control method for the ultrasound treatment device as described above are operated. Therefore, no further details will be given here. In addition, the description of the beneficial effects of adopting the same method will not be described again. For technical details not disclosed in the computer-readable storage medium embodiments involved in the present application, please refer to the description of the method embodiments in the present application. By way of example, program instructions may be deployed for execution on one computing device, on multiple computing devices located at one location, or on multiple computing devices distributed across multiple locations and interconnected by a communications network.

Those skilled in the art can understand that all or part of the processes in the methods of the above embodiments can be completed by instructing relevant hardware through a computer program. The above program can be stored in a computer-readable storage medium, and when the program is executed, the process may include the processes of the embodiments of the above methods. The above-mentioned storage medium can be a magnetic disk, an optical disk, a read-only memory (ROM) or a RAM, etc.

In addition, it should be noted that the device embodiments described above are only illustrative. The units described as separate components may or may not be physically separated, and the components shown as units may or may not be physical units, that is, it can be located in one place, or it can be distributed across multiple network units. Some or all of the modules can be selected according to actual needs to achieve the objective of the solution according to the embodiment. In addition, in the drawings of the device embodiments provided in the present application, the connection relationship between modules indicates that there are communication connections between them, which can be specifically operated as one or more communication buses or signal lines. Those skilled in the art can understand and operate the method without any creative effort.

Through the above description of the embodiments, those skilled in the art can clearly understand that the present application can be operated by software plus necessary general hardware. Of course, it can also be operated by dedicated hardware including dedicated integrated circuits, dedicated CPUs, dedicated memories, dedicated components, etc. In general, all functions performed by computer programs can be easily operated with corresponding hardware. Moreover, the specific hardware structures used to operate the same function can also be diverse, such as analog circuits, digital circuits or special-purpose circuits, etc. However, for the present application, software program operation is a better operation in most cases. Based on this understanding, the technical solution of the present application can be embodied in the form of a software product in essence or that contributes to the related art. The computer software product is stored in a readable storage medium, such as a computer floppy disk., U disk, mobile hard disk, ROM, RAM, magnetic disk or optical disk, etc., including a number of instructions to cause a computer device (which can be a personal computer, a server, or a network device, etc.) to execute the methods of various embodiments of the present application.

The above are only some embodiments of the present application, and are not intended to limit the scope of the present application. Any equivalent structural or process transformations made according to the description and drawings of the present application, or direct/indirect application in other related technical fields are included in the scope of the present application.

The invention claimed is:

1. A control method for an ultrasound treatment device, wherein the ultrasound treatment device comprises:

an ultrasound treatment tip configured to output ultrasound energy;

a displacement sensor provided on the ultrasound treatment tip or a handle portion of the ultrasound treatment device, and configured to collect displacement data of the ultrasound treatment tip; and a contact sensor provided on the ultrasound treatment tip and configured to collect current contact data between the ultrasound treatment tip and corresponding human skin, and wherein the control method comprises:

determining whether the ultrasound treatment tip moves according to current displacement data of the ultrasound treatment tip collected by the displacement sensor;

determining a contact state between the ultrasound treatment tip and the human skin according to the current contact data of the ultrasound treatment tip collected by the contact sensor; and controlling the ultrasound treatment tip to start or stop outputting the ultrasound energy according to the current displacement data and the current contact data;

wherein the contact sensor comprises a pressure sensor, and the current contact data of the ultrasound treatment tip is current pressure data collected by the pressure sensor; and wherein the determining the contact state between the ultrasound treatment tip and the human skin according to the current contact data of the ultrasound treatment tip collected by the contact sensor comprises:

determining a pressure difference between any two adjacent moments within a preset time period to obtain at least two pressure change values according to historical pressure data collected by the pressure sensor and the current pressure data; and determining whether the ultrasound treatment tip slides in the treatment area according to the at least two pressure change values.

2. The control method according to claim 1, wherein the determining the contact state between the ultrasound treatment tip and the human skin according to the current contact data of the ultrasound treatment tip collected by the contact sensor comprises:

in response to determining that the current pressure data is greater than or equal to a preset pressure value, and the current displacement data is greater than 0, controlling the ultrasound treatment tip to output the ultrasound energy.

3. The control method according to claim 1, wherein the determining whether the ultrasound treatment tip slides in the treatment area according to the at least two pressure change values comprises:

in response to all the pressure change values being zero, determining that the ultrasound treatment tip does not slide in the treatment area; and controlling the ultrasound treatment tip to stop outputting the ultrasound energy.

4. The control method according to claim 1, wherein the determining whether the ultrasound treatment tip moves according to the current displacement data of the ultrasound treatment tip collected by the displacement sensor comprises:

obtaining a moving speed value of the ultrasound treatment tip;

determining whether the moving speed value is greater than or equal to a preset moving speed value; and in response to the moving speed value being greater than or equal to the preset moving speed value, determining that the ultrasound treatment tip moves.

5. An ultrasound treatment device, comprising:

an ultrasound treatment tip configured to output ultrasound energy;

a displacement sensor provided on the ultrasound treatment tip or a handle portion of the ultrasound treatment device, and configured to collect displacement data of the ultrasound treatment tip;

a contact sensor provided on the ultrasound treatment tip and configured to collect current contact data between the ultrasound treatment tip and corresponding human skin; and a controller configured to control the ultrasound treatment tip to start or stop outputting the ultrasound energy based on the control method according to claim 1.

6. A non-transitory computer-readable storage medium, wherein a control program for an ultrasound treatment device is stored on the non-transitory computer- readable storage medium, and when the control program for the ultrasound treatment device is executed by a processor, the control method for the ultrasound treatment device according to claim 1 is operated.

* * * * *